United States Patent
Putzig

(10) Patent No.: US 7,795,188 B2
(45) Date of Patent: Sep. 14, 2010

(54) ZIRCONIUM-BASE CROSS-LINKER COMPOSITIONS AND THEIR USE IN HIGH PH OIL FIELD APPLICATIONS

(75) Inventor: Donald Edward Putzig, Newark, DE (US)

(73) Assignee: E.I. du Pont de Nemours and Company

(*) Notice: Subject to any disclaimer, the term of this patent is extended or adjusted under 35 U.S.C. 154(b) by 370 days.

(21) Appl. No.: 11/731,405

(22) Filed: Mar. 30, 2007

(65) Prior Publication Data

US 2008/0236824 A1    Oct. 2, 2008

(51) Int. Cl.
C23F 11/18       (2006.01)
C09K 8/68        (2006.01)
E21B 43/267      (2006.01)
E21B 33/00       (2006.01)
E21B 43/26       (2006.01)

(52) U.S. Cl. .............. 507/271; 507/211; 166/280.1; 166/285; 166/308.3

(58) Field of Classification Search .............. 166/280.1, 166/300, 285, 308.3; 507/203, 219, 211, 507/271
See application file for complete search history.

(56) References Cited

U.S. PATENT DOCUMENTS

| | | | |
|---|---|---|---|
| 2,824,115 A * | 2/1958 | Beacham et al. | 556/56 |
| 2,894,966 A * | 7/1959 | Russell | 556/2 |
| 4,477,360 A | 10/1984 | Almond | |
| 4,579,670 A | 4/1986 | Payne | |
| 4,683,068 A * | 7/1987 | Kucera | 507/201 |
| 4,702,848 A | 10/1987 | Payne | |
| 4,883,605 A | 11/1989 | Putzig | |
| 5,478,802 A | 12/1995 | Moradi-Araghi | |
| 2003/0029615 A1 | 2/2003 | Maberry et al. | |
| 2003/0029616 A1 | 2/2003 | Maberry et al. | |
| 2007/0187098 A1 | 8/2007 | Putzig | |
| 2007/0187101 A1 | 8/2007 | Putzig | |
| 2007/0187102 A1 | 8/2007 | Putzig | |
| 2007/0191236 A1 | 8/2007 | Putzig | |

FOREIGN PATENT DOCUMENTS

WO   WO2007/095367 A   8/2007
WO   WO2008/082504 A   7/2008

OTHER PUBLICATIONS

Technical Bulletin of BASF, www2.basf.us/urethanechemicals/kun_chemicals_case/pdfs/Quadrol.pdf, 2001.*
Technical Bulletin of BASF, www2.basf.us/performancechemical/pdfs/Quadrol_Polyol.pdf, 2002.*
U.S. Appl. No. 11/643,513, filed Dec. 21, 2006, Putzig.
Chaberek et al.; Hydrolytic tendencies of metal chelate compounds. III. Oxometal Ions; Journal of the American Chemical Society, 1959. 61, 515-519.

* cited by examiner

Primary Examiner—Timothy J. Kugel
Assistant Examiner—Aiqun Li
(74) Attorney, Agent, or Firm—Kathryn M. Sanchez

(57) ABSTRACT

A zirconium cross-linking agent produced by a process which comprises contacting a zirconium triethanolamine complex with a mixture of polyols, which mixture comprises a hydroxyalkylated diamine and a hydrocarbon polyol. There is further provided a cross-linking composition which comprises (a) an aqueous liquid, (b) a cross-linkable organic polymer, and (c) a solution of a zirconium cross-linking agent which is produced by a process which comprises contacting a zirconium triethanolamine complex having a molar ratio of 1:2 to 1:5 of zirconium to triethanolamine with a mixture of polyols, which mixture comprises a hydroxyalkylated diamine and a hydrocarbon polyol wherein the molar ratio of zirconium to hydroxyalkylated diamine is 1:0.5 to 1:1 and the molar ratio of zirconium to hydrocarbon polyol is 1:0.5 to 1:1.5. The composition can be used in oil field applications for hydraulic fracturing and plugging of permeable zones and leaks in subterranean formations.

28 Claims, No Drawings

ZIRCONIUM-BASE CROSS-LINKER COMPOSITIONS AND THEIR USE IN HIGH PH OIL FIELD APPLICATIONS

FIELD OF THE INVENTION

The present invention relates to zirconium chelates and their use in oil field applications such as hydraulic fracturing and plugging of permeable zones.

BACKGROUND OF THE INVENTION

The production of oil and natural gas from an underground well (subterranean formation) can be stimulated by a technique called hydraulic fracturing, in which a viscous fluid composition (fracturing fluid) containing a suspended proppant (e.g., sand, bauxite) is introduced into an oil or gas well via a conduit, such as tubing or casing, at a flow rate and a pressure which create, reopen and/or extend a fracture into the oil- or gas-containing formation. The proppant is carried into the fracture by the fluid composition and prevents closure of the formation after pressure is released. Leak-off of the fluid composition into the formation is limited by the fluid viscosity of the composition. Fluid viscosity also permits suspension of the proppant in the composition during the fracturing operation. Polysaccharides and cellulosic polymers or their derivatives are typically used to provide viscosity in these fluids. Cross-linking agents, such as borates, titanates or zirconates, are usually incorporated into the fluid composition to control viscosity.

Typically, less than one third of available oil is extracted from a well after it has been fractured before production rates decrease to a point at which recovery becomes uneconomical. Enhanced recovery of oil from such subterranean formations frequently involves attempting to displace the remaining crude oil with a driving fluid, e.g., gas, water, brine, steam, polymer solution, foam, or micellar solution. Ideally, such techniques (commonly called flooding techniques) provide a bank of oil of substantial depth being driven into a producing well; however, in practice this is frequently not the case. Oil-bearing strata are usually heterogeneous, some parts of them being more permeable than others. As a consequence, channeling frequently occurs, so that the driving fluid flows preferentially through permeable zones depleted of oil (so-called "thief zones") rather than through those parts of the strata which contain sufficient oil to make oil-recovery operations profitable.

Difficulties in oil recovery due to thief zones may be corrected by injecting an aqueous solution of an organic polymer and a cross-linking agent into a subterranean formation under conditions where the polymer will be cross-linked to produce a gel, thus reducing permeability of the subterranean formation to driving fluid (gas, water, etc.). Polysaccharide- or partially hydrolyzed polyacrylamide-based fluids cross-linked with certain aluminum, titanium, zirconium, and boron based compounds are used in these enhanced oil recovery applications.

Cross-linked fluids or gels, whether for fracturing a subterranean formation or for reducing permeability of zones in subterranean formation, are now being used in hotter and deeper wells under a variety of temperature and pH conditions, where rates of cross-linking with known cross-linking compositions may be unacceptable.

U.S. Pat. No. 4,477,360 discloses a cross-linking composition comprising a zirconium salt or chelate and a polyhydroxyl-containing compound having from about 3 to about 7 carbon atoms, and optionally an aqueous fluid or an alkanol, for use in fracturing a subterranean formation. While this composition provides a rate of cross-linking that is often desirable in hotter, deeper wells, it provides insufficient initial viscosity development to carry sand into the formation to the extent desired.

U.S. Pat. No. 4,883,605 discloses a water-soluble zirconium chelate formed from a tetraalkyl zirconate and hydroxyethyl-tris-(2-hydroxypropyl)ethylenediamine, and the use of the chelate as a cross-linking agent in hydraulic fracturing fluids and in gels that are used for selectively plugging permeable zones in subterranean formations or for plugging subterranean leaks. Co-pending U.S. patent application Ser. No. 11/643,513, filed Dec. 21, 2006, discloses a related complex having a 1:1 molar ratio of zirconium and N,N,N',N'-tetrakis-(2-hydroxypropyl)-ethylenediamine.

The products of U.S. Pat. No. 4,883,605 and U.S. patent application Ser. No. 11/643,5513 may be used as cross-linkers for use in many hotter, deeper oil well applications. However, at high pH conditions (such as pH 10), where polysaccharides are most stable, the products of U.S. Pat. No. 4,883,605 cross-link too slowly (>10 minutes), causing a "sand out" to occur, which is the result of sand depositing at the bottom of the wellbore due to lack of viscosity development before the gel reaches the fracture zone. The products of co-pending U.S. patent application Ser. No. 11/643,513 cross-link in the desirable range, which is 3-8 minutes, as illustrated by testing in a FANN viscometer at 275° F. (135° C.) and 122 rpm at 212 reciprocal second of shear. (The FANN results provide a means to predict performance in oil well operation.) Although the products of co-pending U.S. patent application Ser. No. 11/643,513 can be used in many hotter, deeper wells, they do not generate as high a viscosity as desired to maintain the sand in suspension for the length of time needed in hotter, deeper wells having high pH.

Commercially available zirconate cross-linkers, such as tetra-triethanolamine zirconate cross-link too fast under high pH conditions, causing a significant loss in viscosity due to shear degradation, which can also result in a sand out. Nonetheless, it is desirable to use a cross-linking composition at pH 10 or higher, where polysaccharides used in cross-linking compositions are most stable.

There is a need for compositions which cross-link at a rate intermediate between zirconium complexes of hydroxyethyl-tris-(2-hydroxypropyl)ethylenediamine and triethanolamine zirconates, and generate and maintain sufficient viscosity to be used successfully at high pH (about pH 10 and above) and high temperature (325°-400° F., 163-204° C.) conditions.

SUMMARY OF THE INVENTION

The present invention provides an effective cross-linking agent which is a modified zirconium triethanolamine complex, produced by a process which comprises contacting a zirconium triethanolamine complex having a molar ratio of 1:2 to 1:5 of zirconium to triethanolamine with a mixture of polyols, which mixture comprises a hydroxyalkylated diamine and a hydrocarbon polyol. The molar ratio of zirconium to hydroxyalkylated diamine is 1:0.5 to 1:1. The molar ratio of zirconium to hydrocarbon polyol is 1:0.5 to 1:1.5. The temperature for the contacting step can be in the range of 25° C. to 90° C. The reaction is typically performed in the presence of an organic solvent.

The present invention further provides a cross-linking composition which comprises (a) an aqueous liquid, (b) a cross-linkable organic polymer, and (c) a solution of a zirconium cross-linking agent which is produced by a process which comprises contacting a zirconium triethanolamine complex having a molar ratio of 1:2 to 1:5 of zirconium to triethanolamine with a mixture of polyols, which mixture comprises a hydroxyalkylated diamine and a hydrocarbon polyol wherein the molar ratio of zirconium to hydroxyalkylated diamine is 1:0.5 to 1:1 and the molar ratio of zirconium to hydrocarbon polyol is 1:0.5 to 1:1.5. Optionally, a solvent may be further added to the cross-linking composition.

The cross-linking composition of this invention is useful in oil field applications, for example, for hydraulically fracturing a subterranean formation using the composition. The composition of this invention is further useful for plugging permeable zones or leaks in a subterranean formation. The components of the cross-linking composition may be mixed prior to introducing them into the formation or the components can be introduced and permitted to react in the formation after a controllable period of time.

Surprisingly, in view of known cross-linking compositions comprising zirconium-triethanolamine complexes, the cross-linking composition of this invention has a desirable cross-linking rate of 5-7 minutes generating good viscosity, preferably in the range of 500 to 1000 centipoise (cp) after 90 minutes at pH 10 by simulation in a FANN viscometer at 275° F. (135° C.) and 212 rpm at 100 reciprocal second of shear. If viscosity is too high, gel syneresis occurs wherein there is over-cross-linking of the polymer and water separates from the gel causing globules of the gel to form, which can no longer suspend the sand or other proppant.

This invention provides a method for hydraulically fracturing a subterranean formation which comprises using a cross-linking composition as described herein. This method comprises introducing into a subterranean formation at a flow rate and pressure sufficient to create, reopen and/or extend a fracture in the formation, (a) an aqueous liquid, (b) a cross-linkable organic polymer, and (c) a solution of a zirconium cross-linking agent which is produced by a process which comprises contacting a zirconium triethanolamine complex having a molar ratio of 1:2 to 1:5 of zirconium to triethanolamine with a mixture of polyols, which mixture comprises a hydroxyalkylated diamine and a hydrocarbon polyol wherein the molar ratio of zirconium to hydroxyalkylated diamine is 1:0.5 to 1:1 and the molar ratio of zirconium to hydrocarbon polyol is 1:0.5 to 1:1.5.

This invention provides a method for plugging a permeable zone or leak in a subterranean formation which comprises introducing into said zone or said leak, (a) an aqueous liquid, (b) a cross-linkable organic polymer, and (c) a solution of a zirconium cross-linking agent which is produced by a process which comprises contacting a zirconium triethanolamine complex have a molar ratio of 1:2 to 1:5 of zirconium to triethanolamine with a mixture of polyols, which mixture comprises a hydroxyalkylated diamine and a hydrocarbon polyol wherein the molar ratio of zirconium to hydroxyalkylated diamine is 1:0.5 to 1:1 and the molar ratio of zirconium to hydrocarbon polyol is 1:0.5 to 1:1.5.

The present invention provides methods for effective viscosity generation in oil field applications such as fluid fracturing and plugging permeable zones. Surprisingly, the cross-linking composition of this invention cross-links to achieve maximum viscosity in a desirable 5 to 7 minute range at well temperatures of 121-204° C. (250-400° F.), especially at temperatures of 163-204° C. (325-400° F.), whereas in general, triethanolamine zirconium complexes have rates of cross-linking that are too fast, or when combined with large volumes of water or at high mole ratios of triethanolamine: zirconium, the rates of cross-linking of triethanolamine zirconium complexes are too slow.

DETAILED DESCRIPTION OF THE INVENTION

Trademarks and trade names used herein are shown in upper case.

This invention provides an effective cross-linking agent or cross-linker for use in cross-linking compositions for oil field applications. More specifically, it provides a solution of a zirconium cross-linking agent, which is a modified zirconium triethanolamine complex, which has a rate of cross-linking in a desired 5-7 minute range (in a FANN viscometer at 275° F. (135° C.) and 212 rpm at 100 reciprocal second of shear), indicating good performance at high pH and high temperature conditions. Surprisingly, a cross-linking composition comprising the zirconium cross-linking agent solution provides higher initial viscosity development than those cross-linking agents and compositions which comprise mixtures of zirconium triethanolamine, glycerol and water. The modified zirconium complex is produced by a process which comprises contacting a zirconium triethanolamine complex with a mixture of polyols, which mixture comprises a hydroxyalkylated ethylenediamine and a hydrocarbon polyol.

Zirconium triethanolamine complex solution may be purchased as TYZOR TEAZ organic zirconate, available from E.I. du Pont de Nemours and Company, Wilmington, Del. Alternatively, a solution of triethanolamine zirconate complex can be prepared by a process which comprises contacting a solution of a tetraalkyl zirconate in a $C_1$-$C_6$ alcohol with two to five molar equivalents of triethanolamine (TEA) to produce a reaction product, which is a solution of triethanolamine zirconate complex. Preferably the molar ratio of TEA to zirconium is about 4:1. A number of tetraalkyl zirconates (also known as zirconium tetraalkoxides) can be used to prepare the solution of triethanolamine zirconate complex used in the present invention, e.g., tetra-1-propyl zirconate, tetra-n-propyl zirconate, and tetra-n-butyl zirconate. The preferred tetraalkyl zirconate is tetra-n-propyl zirconate, available as TYZOR NPZ organic zirconate, a solution in n-propanol, with a zirconium content as $ZrO_2$ of about 28% by weight, available from E.I. du Pont de Nemours and Company, Wilmington, Del.

The solution of triethanolamine zirconate complex is then modified by contacting the solution with from about 0.5 to about 1.0 moles molar equivalents of a hydroxyalkylated ethylenediamine and from about 0.5 to about 1.5 molar equivalents of hydrocarbon polyol, each molar ratio based on 1 mole of zirconium. Outside of these ranges, undesirable behavior, such as poor cross-linking rates may occur. Higher amounts of polyol cause gelling of the zirconium cross-linking agent. Conveniently and preferably the hydroxyalkylated ethylenediamine is N,N,N',N'-tetrakis-(2-hydroxypropyl)ethylenediamine. This diamine is available commercially, for example, from BASF Corporation, Mount Olive, N.J., under the name QUADROL polyol. Examples of hydrocarbon polyols include glycerol, sorbitol and erythritol. Conveniently and preferably, the hydrocarbon polyol is glycerol. Contacting triethanolamine zirconate complex with hydroxyalkylated ethylenediamine and hydrocarbon polyol can be performed at a range of temperatures, e.g., between 25° C. and 90° C., preferably between 50° C. and 80° C.

The present invention also provides a cross-linking composition which comprises (a) an aqueous liquid; (b) a cross-linkable organic polymer; and (c) a solution comprising the reaction product of contacting triethanolamine zirconate complex having a molar ratio of 1:2 to 1:5 of zirconium to triethanolamine, preferably a ratio of 1:4, with a hydroxylated diamine at a molar ratio of 0.5:1 to 1:1 of diamine to zirconium and a hydrocarbon polyol at a molar ratio of 0.5:1 to 1.5:1 of polyol to zirconium. Optionally a solvent may be present in the solution.

The aqueous liquid (a) is typically selected from the group consisting of water, aqueous salt solutions, and mixed water/organic solvent. Organic solvents that may be used include alcohols, glycols, polyols, and hydrocarbons such as diesel. Preferably, the aqueous liquid is water, aqueous methanol, aqueous ethanol, or an aqueous solution of a clay stabilizer. Clay stabilizers include, for example, hydrochloric acid and chloride salts, such as, tetramethylammonium chloride (TMAC) or potassium chloride. Preferred stabilizers are TMAC and potassium chloride.

The cross-linking composition further comprises a cross-linkable organic polymer (b). Suitable cross-linkable organic polymers are selected from the group consisting of solvatable polysaccharides, polyacrylamides and polymethacrylamides. Preferably the organic polymer is a solvatable polysaccharide and is selected from the group consisting of gums, gum derivatives and cellulose derivatives. Gums include guar gum and locust bean gum, as well as other galactomannan and glucomannan gums, such as those derived from sennas, Brazilwood, tera, honey locust, karaya gum and the like. Gum derivatives include hydroxyethylguar (HEG), hydroxypropylguar (HPG), carboxyethylhydroxyethylguar (CEHEG), carboxymethylhydroxypropylguar (CMHPG), carboxymethyl guar (CMG), and the like. Cellulose derivatives include those containing carboxyl groups, such as carboxymethylcellulose (CMC), carboxymethylhydroxyethylcellulose (CMHEC), and the like. The solvatable polysaccharides can be used individually or in combination; usually, however, a single material is used. Guar derivatives and cellulose derivatives are preferred, such as, HPG, CMC and CMHPG. HPG is generally more preferred based upon its commercial availability and desirable properties. However, CMC and CMHPG may be more preferred in cross-linking compositions when the pH of the composition is less than 6.0 or higher than 9.0, or when the permeability of the formation is such that one wishes to keep the residual solids at a low level to prevent damage to the formation.

The solution (c) is the solution comprising the reaction product of contacting triethanolamine zirconate complex having a molar ratio of 1:2 to 1:5 of zirconium to triethanolamine, with a hydroxylated diamine and a hydrocarbon polyol, as described hereinabove. Optionally this solution may contain an added organic solvent. Organic solvents that may be used include, for example, alcohols, glycols, and polyols.

The cross-linkable polymer is normally mixed with the aqueous liquid such as water or mixed water/organic solvent or with an aqueous solution to form a base gel. As an example, the aqueous liquid is selected from the group consisting of water, aqueous alcohol (e.g., where the alcohol is methanol or ethanol), and an aqueous solution comprising a clay stabilizer. Clay stabilizers include, for example, hydrochloric acid and chloride salts, such as, tetramethylammonium chloride (TMAC) or potassium chloride. Aqueous solutions comprising clay stabilizers may comprise, for example, 0.05 to 0.5 weight % of the stabilizer, based on the total weight of the cross-linking composition.

The composition may comprise optional components, including those which are common additives for oil field applications. Thus, the composition may further comprise one or more of proppants, friction reducers, bactericides, hydrocarbons, chemical breakers, stabilizers, surfactants, formation control agents, and the like. Proppants include sand, bauxite, glass beads, nylon pellets, aluminum pellets and similar materials. Friction reducers include polyacrylamides. Hydrocarbons include diesel oil. Chemical breakers break the cross-linked polymer (gel) in a controlled manner and include enzymes, alkali metal persulfate, and ammonium persulfate. Stabilizers include clay stabilizers such as hydrochloric acid and chloride salts, for example, tetramethylammonium chloride (TMAC) or potassium chloride. Stabilizers may also include methanol, alkali metal thiosulfate, and ammonium thiosulfate.

These optional components are added in an effective amount sufficient to achieve the desired cross-linking performance based on the individual components, desired cross-linking time, temperature and other conditions present in the formation being fractured or permeable zone being plugged.

The base gel may further comprise an effective amount of a pH buffer to control pH. In the present invention, the buffer is preferably a sodium carbonate or sodium hydroxide-based buffer, which provides a pH of 9-12, preferably about pH 10. Other suitable pH buffers can be used, as are known to those skilled in the art. Less preferred are acidic or neutral pH buffers. For example, in a composition for use at pH of about 4-5, an acetic acid-based buffer can be used. In a composition for use at a pH of 5-7, a fumaric acid-based buffer or a sodium diacetate-based buffer can be used. In a composition for use at a pH of 7-8.5, a sodium bicarbonate-based buffer can be used.

The cross-linking composition is produced by mixing the solution of zirconium complex with the other components, in any order. For example, in one particular application in an oil field, the solution of zirconium complex and optional components are introduced into a formation, while the cross-linkable organic polymer and aqueous liquid are introduced into the formation as a separate stream. Alternatively, all components may be premixed and introduced into a subterranean formation as a single stream. Advantageously, the components may be mixed in different combinations, and more advantageously, the components may be mixed just prior to use to enable easy variation and adjustment of the cross-linking rate.

This invention provides a method for hydraulically fracturing a subterranean formation, which comprises introducing into the formation at a flow rate and pressure sufficient to create, reopen, and/or extend one or more fractures in the formation, a cross-linking composition comprising an aqueous liquid, a cross-linkable organic polymer, and a solution of a zirconium cross-linking agent which is produced by a process which comprises contacting a zirconium triethanolamine complex having a molar ratio of 1:2 to 1:5 of zirconium to triethanolamine with a mixture of polyols, which mixture comprises a hydroxyalkylated diamine and a hydrocarbon polyol wherein the molar ratio of zirconium to hydroxyalkylated diamine is 1:0.5 to 1:1 and the molar ratio of zirconium to hydrocarbon polyol is 1:0.5 to 1:1.5. Optionally, the solution of a zirconium cross-linking agent comprises a solvent and other optional components.

In one embodiment of the method for hydraulically fracturing a subterranean formation, the solution of zirconium cross-linking agent and the cross-linkable polymer are contacted prior to their introduction into the formation, such that the cross-linking agent and polymer react to form a cross-linked gel. The gel is then introduced into the formation at a flow rate and pressure sufficient to create, reopen, and/or extend a fracture in the formation.

A base gel is prepared by mixing the cross-linkable organic polymer with the aqueous liquid. A cross-linked gel is prepared by mixing at a temperature of 50° C. to 90° C., the base gel with a solution of a zirconium cross-linking agent produced by contacting zirconium triethanolamine complex with a mixture of polyols, comprising a hydroxyalkylated diamine in a molar ratio of 1:0.5 to 1:1 of zirconium to diamine and a hydrocarbon polyol in a molar ratio of 1:0.5 to 1:1.5 of zirconium to polyol. Optionally the solution of zirconium cross-linking agent may contain an added solvent. The base gel may further comprise a pH buffer.

Alternatively, the subterranean formation may be penetrated by a wellbore, such that contacting the solution of zirconium cross-linking agent with the base gel occurs in the wellbore and the cross-linked gel is introduced into the formation from the wellbore. This method of hydraulically fracturing a subterranean formation penetrated by a wellbore comprises (a) preparing a base gel by mixing a cross-linkable organic polymer with an aqueous liquid; (b) introducing the base gel into the wellbore; (c) simultaneously with or sequentially after, introducing the base gel into the wellbore, introducing a solution comprising a zirconium cross-linking agent comprising triethanolamine zirconate solution modified with a hydroxyalkylated diamine and polyol as described previously; (d) permitting the base gel and the solution of zirconium cross-linking agent to react to form a cross-linked aqueous gel; and (e) introducing the cross-linked gel into the formation from the wellbore at a flow rate and pressure sufficient to create, reopen, and/or extend a fracture in the formation. A pH buffer may be independently admixed with the base gel prior to introducing the base gel into the wellbore.

Upon creation of a fracture or fractures, the method may further comprise introducing a cross-linking composition comprising the solution of zirconium cross-linking agent, a cross-linkable organic polymer and proppant into the fracture or fractures. This second introduction of a solution of zirconium cross-linking agent is preferably performed in the event the cross-linking composition used to create the fracture or fractures did not comprise proppant.

Another use for the solution of zirconium complex of the present invention relates to a method for selectively plugging permeable zones and leaks in subterranean formations which comprises introducing into the permeable zone or the site of the subterranean leak, a cross-linking composition comprising an aqueous liquid, a cross-linkable organic polymer, and a solution of a zirconium cross-linking agent which is produced by a process which comprises contacting a zirconium triethanolamine complex having a molar ratio of 1:2 to 1:5 of zirconium to triethanolamine with a mixture of polyols, which mixture comprises a hydroxyalkylated diamine and a hydrocarbon polyol wherein the molar ratio of zirconium to hydroxyalkylated diamine is 1:0.5 to 1:1 and the molar ratio of zirconium to hydrocarbon polyol is 1:0.5 to 1:1.5, into the permeable zone or the site of the subterranean leak.

In a first embodiment of the method for plugging a permeable zone or a leak in a subterranean formation, the aqueous liquid, cross-linkable organic polymer and the solution of zirconium cross-linking agent are contacted prior to their introduction into the subterranean formation, such that the polymer and zirconium cross-linking agent react to form a cross-linked aqueous gel, which gel is then introduced into the formation.

In an alternative embodiment of the method for plugging a permeable zone or a leak in a subterranean formation, the solution of zirconium cross-linking agent and the cross-linkable organic polymer are introduced separately, either simultaneously or sequentially, into the permeable zone or the site of the subterranean leak such that cross-linking occurs within the subterranean formation. This method comprises (a) preparing a base gel by mixing a cross-linkable organic polymer with an aqueous liquid; (b) introducing the base gel into the into the permeable zone or the site of the subterranean leak; (c) simultaneously with or sequentially after, introducing the base gel into the into the permeable zone or the site of the subterranean leak, introducing the solution of zirconium cross-linking agent into the into the permeable zone or the site of the subterranean leak; (d) permitting the base gel and the cross-linking agent to react to form a cross-linked aqueous gel to plug the zone and/or leak. The base gel may further comprise a pH buffer.

The relative amounts of cross-linkable organic polymer and the zirconium complex may vary. One uses small but effective amounts which for both will vary with the conditions, e.g., the type of subterranean formation, the depth at which the method (e.g., fluid fracturing, permeable zone plugging or leak plugging) is to be performed, temperature, pH, etc. Generally one uses as small an amount of each component as will provide the viscosity level necessary to effect the desired result, i.e., fracturing of the subterranean formation, or plugging permeable zones or leaks to the extent necessary to promote adequate recovery of oil or gas from the formation.

For example, satisfactory gels can generally be made for fluid fracturing by using the cross-linkable organic polymer in amounts up to about 1.2 weight % typically in the range of 0.1 to 1.2 weight %, based on the total weight of the gel. The cross-linking composition is used in amounts that provide 0.01 to 0.50 weight % of the zirconium cross-linking agent (zirconium complex), based on the total weight of the gel. Preferably, from about 0.25 to about 0.75 weight % of the cross-linkable organic polymer is used and from about 0.05 to about 0.25 weight % of the zirconium complex is used.

In a method for plugging permeable zones or leaks, generally about 0.25 to 1.2 weight % of a cross-linkable organic polymer is used, preferably 0.40 to 0.75 weight %, based on the total weight of the gel. Generally about 0.01 to 0.50 weight % of the zirconium cross-linking agent (zirconium complex) is used, preferably 0.05 to 0.25 weight %, based on the total weight of the gel.

The amount of zirconium complex used to cross-link the organic polymer is that which provides a zirconium ion concentration in a range from about 0.0005 weight % to about 0.1 weight %, based on the total weight. The preferred concentration of zirconium ion is in the range of from about 0.001-0.05 weight %, based on the total weight.

Typically the solution of zirconium complex of this invention can be used at a pH of from about 3 to 11. For low temperature applications (150-250° F., 66-121° C.), carbon dioxide-based energized fluids may be used. In this case, a pH for the cross-linking composition of about 3 to about 6 is preferred. For moderate or high temperature applications (250-400° F., 121-204° C.), a pH of about 9 to about 11 is preferred. Advantageously, the solution of zirconium cross-linking agent of this invention is used at a temperature of 275-400° F. (135-204° C.), more advantageously at a temperature of 325-400° F. (163-204° C.) and at pH 9-11, preferably at pH about 10.

EXAMPLES

The preparation of the compositions in the Examples and in the Controls were each carried out in closed vessels containing an agitator, thermometer, condenser, nitrogen inlet and dropping funnel. Unless specified otherwise, percentages are given by weight. Temperatures are given in degrees Celsius. The cross-linking properties of the compositions of this invention are given in the Examples as a function of the viscosity of carboxymethyl, hydroxypropylguar cross-linked with the zirconate of this invention.

Comparative Example A

A 500 ml flask, equipped with a thermocouple, dropping funnel, N2 bleed and condenser, was charged with 156.8 g of TYZOR TEAZ organic zirconate. Agitation was started and a mixture of 21 g of glycerol and 21 g of water were added. The solution was agitated for 2 hours at 60° C. to give 190.2 g of an orange solution containing 10.4% Zr.

Comparative Example B

Triethanolamine (135.2 g) was added to 100 g of tetra-n-propyl zirconate solution (TYZOR NPZ organic zirconate, available from E.I. du Pont de Nemours and Company, Wilmington, Del.). The reaction mixture was heated to 60° C. and held there for 4 hours. Upon completion of the reaction the resultant solution of tetra(triethanolamine) zirconate was concentrated on a rotary evaporator under reduced pressure to yield 155 g of a viscous yellow oil, which contained 13.2% Zr.

Comparative Example C

Hydroxyethyl tris-2-hydroxypropyl ethylenediamine (L-699) (146 g) was added to 220.3 g of tetra-n-propyl zirconate. The reaction mixture was heated to 60° C. and held there for 4 hours to give 346 g of a pale yellow liquid containing hydroxyethyl-tris-2-hydroxypropyl ethylenediamine zirconate, containing 12.4% Zr.

Comparative Example D

A 500 ml flask, equipped with a thermocouple, dropping funnel, N2 bleed and condenser, was charged with 100 g of TYZOR NPZ organic zirconate. Agitation was started and 135.3 g of triethanolamine was added. The mixture was heated for 2 hours at 60° C. and then 33.2 g of QUADROL polyol were added. The solution was heated at 60° C. for another 2 hours to give 268 g of a stable solution containing 7.7% Zr.

Comparative Example E

A 500 ml flask, equipped with a thermocouple, dropping funnel, N2 bleed and condenser, was charged with 100 g of TYZOR NPZ organic zirconate. Agitation was started and 135.3 g of triethanolamine were added. The mixture was heated for 2 hours at 60° C. and then 66.3 g of QUADROL polyol were added. The solution was heated at 60° C. for another 2 hours to give 300 g of a stable solution containing 6.9% Zr.

Example 1

A 500 ml flask, equipped with a thermocouple, dropping funnel, N2 bleed and condenser, was charged with 100 g of TYZOR NPZ organic zirconate. Agitation was started and 135.3 g of triethanolamine were added. The solution was heated to 60° C. and held for 2 hours. Then 33.2 g of QUADROL polyol were added and the solution was held at 60° C. for another 2 hours. Next, 10.5 g of glycerol were added and the solution was agitated for an additional 2 hours at 60° C. to give 279 g of an orange solution containing 7.4% Zr.

Example 2

A 500 ml flask, equipped with a thermocouple, dropping funnel, N2 bleed and condenser, was charged with 100 g of TYZOR NPZ organic zirconate. Agitation was started and 135.3 g of triethanolamine were added. The solution was heated to 60° C. and held for 2 hours. Then 33.2 g of QUADROL polyol were added and the solution was held at 60° C. for another 2 hours. Next, 21 g of glycerol were added and the solution was agitated for an additional 2 hours at 60° C. to give 289 g of an orange solution containing 7.2% Zr.

Example 3

A 500 ml flask, equipped with a thermocouple, dropping funnel, N2 bleed and condenser, was charged with 100 g of TYZOR NPZ organic zirconate. Agitation was started and a mixture of 135.2 g of triethanolamine and 66.3 g of QUADROL polyol were added. The solution was heated to 60° C. and held there 2 hours. Then 10.5 g of glycerol were added and the solution was agitated for an additional 2 hours at 60° C. to give 312 g of an orange solution containing 6.6% Zr.

Example 4

A 500 ml flask, equipped with a thermocouple, dropping funnel, N2 bleed and condenser, was charged with 100 g of TYZOR NPZ organic zirconate. Agitation was started and 135.3 g of triethanolamine were added. The solution was heated to 60° C. and held for 2 hours. Then 66.3 g of QUADROL polyol were added and the solution was held at 60° C. for another 2 hours. Next, 21 g of glycerol were added and the solution was agitated for an additional 2 hours at 60° C. to give 322 g of an orange solution containing 6.4% Zr.

Example 5

A 500 ml flask, equipped with a thermocouple, dropping funnel, N2 bleed and condenser, was charged with 100 g. of TYZOR NPZ organic zirconate. Agitation was started and 135.3 g of triethanolamine were added. The solution was heated to 60° C. and held for 2 hours. Then 33.2 g of QUADROL polyol were added and the solution was held at 60° C. for another 2 hours. Next, 42 g of glycerol were added. The solution gelled after most of the glycerol was added.

Example 6

A 500 ml flask, equipped with a thermocouple, dropping funnel, N2 bleed and condenser, was charged with 100 g of TYZOR NPZ organic zirconate. Agitation was started and 135.3 g of triethanolamine were added. The solution was heated to 60° C. and held for 2 hours. Then 66.3 g of QUADROL polyol were added and the solution was held at 60° C. for another 2 hours. Next, 42 g of glycerol were added. The solution gelled after most of the glycerol was added.

Preparation of Base Gel

A Waring blender jar was filled with 1 liter of distilled water. To this was added 2 g of a 50% aqueous solution of tetramethylammonium chloride clay stabilizer. Agitation was started and 3.6 g of carboxymethylhydroxypropylguar (CM-HPG) was sprinkled into the vortex of the agitating solution. The pH of the resultant slurry was adjusted to 6 with sodium diacetate and agitation continued for 30 minutes. The pH was then adjusted to 10.3 with 10% sodium hydroxide solution. Agitation was stopped and the gel was allowed to stand for 30 minutes or more before use.

Viscosity Measurement of Zirconate Cross-Linked Base Gel

To 250 ml of a vigorously agitated sample of base gel in a Waring blender jar, was added 0.00032 moles of zirconium (0.2-1.0 ml dependent on percent zirconium of cross-linker solution—hereinafter referred to as the Standard Loading Density). Agitation was continued for about 15-180 seconds. A 25 ml sample of the cross-linker containing gel was placed in the cup of the FANN 50 Viscometer with an R-1, B-3 configuration and viscosity was measured at 275° F. (135° C.) and 122 rpm at 212 reciprocal seconds of shear.

Table 1 shows the performance of a 30 lb/1000 gallon (3600 g/1000 liters) CMHPG gel cross-linked with both known zirconates (Controls) and those of the invention. In this Table, "Zr, %" refers to the weight percent of zirconium in the zirconium solutions produced in Controls and Examples. "Zr, soln., ml" refers to the volume of zirconium complex solution added to the base gel. "Zr, moles" refers to the number of moles of Zr added to the base gel. "Alkanol amine" refers to the alkanol amine added; TEA is triethanolamine; "L-699" is hydroxyethyl-tris-(2-hydroxyisopropyl) ethylenediamine. Moles of alkanol amine added are provided in parentheses. "Hydroxyl alkylated amine" refers to the hydroxylated amine added, wherein in these examples, the hydroxylated amine is QUADROL polyol. Moles of added the hydroxylated amine added are provided in parentheses. "Water (moles)" refers to the amount of water added, with moles in parentheses. "Fann Time max" means the time, in minutes, for the cross-linked gel to reach maximum viscosity, after zirconium solution is added to base gel. "Viscosity @ time max" means the maximum viscosity, in centipoise (cp) that is reached at Fann Time max. "Viscosity @ 90 min." means the viscosity, in cp, of the gel 90 minutes after zirconium solution is added to base gel.

shear degradation and loss of viscosity of the cross-linked gel would occur, prior to reaching the zone to be fractured or plugged in the formation.

However, the rate of cross-linking for the hydroxyethyl-tris-2-hydroxypropyl ethylenediamine zirconium complex of Comparative Example C (U.S. Pat. No. 4,883,605) is very slow. In the field, viscosity generation is so slow at the slow rate of cross-linking, that sand would be expected to drop out of the cross-linking fluid before the fluid reached the zone to be fractured.

The rate of cross-linking for the triethanolamine zirconium complex of CH-3168 (Comparative Examples D and E) generates excellent viscosity, however its rate of cross-linking is too fast for the higher temperature wells. In the field, this would result in sand being deposited prematurely, causing less than desired oil recovery.

The cross-linking rates containing the solutions of this invention in Examples 1-4 are within the desirable range of 5-7 minutes and viscosity development and retention is excellent. At these cross-linking rates, the cross-linking compositions can be used in the field for fracturing or plugging, even for hotter, deeper formations.

Comparative Examples F and G show that the use of 2 moles of polyol caused the zirconium complex solution to gel toward the end of the addition.

What is claimed is:

1. A cross-linking composition which comprises (a) an aqueous liquid, (b) a cross-linkable organic polymer, and (c) a solution of a zirconium cross-linking agent which is produced by a process which comprises contacting a zirconium triethanolamine complex having a molar ratio of 1:2 to 1:5 of zirconium to triethanolamine with a mixture of polyols, which mixture comprises a hydroxyalkylated diamine and a

TABLE 1

Performance Results

| Example No. | Zr, % | Zr soln., ml | Zr, moles | Alkanol amine (moles) | Hydroxyl alkylated diamine (moles) | Polyol (moles) | Water (moles) | Fann Time max., min. | Viscosity, @ time max., cp | Viscosity, @ 90 min., cp |
|---|---|---|---|---|---|---|---|---|---|---|
| Comp. Ex. A | 10.4 | 0.29 | 1 | TEA (4) | | glycerol (1) | 5.12 | 7 | 560 | 375 |
| Comp. Ex. B | 13.2 | 0.18 | 1 | TEA (4) | | | | 1.5 | 1125 | 660 |
| Comp. Ex. C | 12.4 | 0.27 | 1 | L-699 (1) | | | | 12 | 300 | 225 |
| Comp. Ex. D | 7.7 | 0.39 | 1 | TEA (4) | QUADROL (0.5) | | | 4 | 1375 | 925 |
| Comp. Ex. E | 6.9 | 0.43 | 1 | TEA (4) | QUADROL (1) | | | 3 | 800 | 610 |
| Ex. 1 | 7.4 | 0.4 | 1 | TEA (4) | QUADROL (0.5) | glycerol (0.5) | | 5 | 1025 | 680 |
| Ex. 2 | 7.2 | 0.42 | 1 | TEA (4) | QUADROL (0.5) | glycerol (1) | | 6.5 | 820 | 430 |
| Ex. 3 | 6.6 | 0.40 | 1 | TEA (4) | QUADROL (1) | glycerol (0.5) | | 5 | 1100 | 700 |
| Ex. 4 | 6.4 | 0.46 | 1 | TEA (4) | QUADROL (1) | glycerol (1) | | 6.5 | 615 | 425 |
| Comp. Ex. F | | | 1 | TEA (4) | QUADROL (0.5) | glycerol (2) | gelled | | | |
| Comp. Ex. G | | | 1 | TEA (4) | QUADROL (1) | glycerol (2) | gelled | | | |

As can be seen from the Table, the rate of cross-linking for the triethanolamine zirconium complex of U.S. Pat. No. 4,477,360 (Comparative Example A) cross-links in the desirable 3-8 minute range, however viscosity development and retention is less than desired for the highest temperature wells. In the field, this would result in sand being deposited prematurely, causing less than desired oil recovery.

The zirconium-triethanolamine cross-linking composition in Comparative Example B generates excellent viscosity; however its rate of cross-linking, as measured by time to reach maximum viscosity, is much too fast at 1.5 minutes. In the field, at this rate of cross-linking, it would be expected that hydrocarbon polyol wherein the molar ratio of zirconium to hydroxyalkylated diamine is 1:0.5 to 1:1 and the molar ratio of zirconium to hydrocarbon polyol is 1:0.5 to 1:1.5 and wherein the cross-linking composition has a cross-linking rate of 5-7 minutes generating viscosity in the range of 500 to 1000 centipoise (cp) after 90 minutes at pH 10 by simulation in a FANN viscometer at 275° F. (135° C.) and 212 rpm at 100 reciprocal second of shear.

2. The cross-linking composition of claim 1 wherein the hydroxyalkylated diamine is N,N,N',N'-tetrakis-(2-hydroxypropyl)ethylenediamine and the hydrocarbon polyol is glycerol.

3. The cross-linking composition of claim 2 wherein the cross-linkable organic polymer is a solvatable polysaccharide.

4. The cross-linking composition of claim 3 wherein the cross-linkable organic polymer is selected from the group consisting of gums, gum derivatives and cellulose derivatives.

5. The cross-linking composition of claim 4 wherein the cross-linkable organic polymer is hydroxypropylguar, carboxymethylhydroxypropylguar, or carboxymethylcellulose.

6. The cross-linking composition of claim 1 further comprising a solvent.

7. The cross-linking composition of claim 1 wherein the cross-linkable polymer is mixed with the aqueous liquid to form a base gel and wherein the base gel comprises a pH buffer.

8. The cross-linking composition of claim 7 wherein the pH buffer is a sodium carbonate or sodium hydroxide-based buffer and pH is controlled at pH 9 to 12.

9. The cross-linking composition of claim 1 wherein the aqueous liquid is selected from the group consisting of water, aqueous salt solutions and mixed water/organic solvent.

10. The cross-linking composition of claim 9 wherein the aqueous liquid is water, aqueous methanol, aqueous ethanol, an aqueous solution of tetramethylammmonium chloride or an aqueous solution of potassium chloride.

11. A method for hydraulically fracturing a subterranean formation which comprises introducing into a subterranean formation at a flow rate and pressure sufficient to create, reopen and/or extend a fracture in the formation, (a) an aqueous liquid, (b) a cross-linkable organic polymer, and (c) a solution of a zirconium cross-linking agent which is produced by a process which comprises contacting a zirconium triethanolamine complex having a molar ratio of 1:2 to 1:5 of zirconium to triethanolamine with a mixture of polyols, which mixture comprises a hydroxyalkylated diamine and a hydrocarbon polyol wherein the molar ratio of zirconium to hydroxyalkylated diamine is 1:0.5 to 1:1 and the molar ratio of zirconium to hydrocarbon polyol is 1:0.5 to 1:1.5, and wherein the cross-linking composition has a cross-linking rate of 5-7 minutes generating viscosity in the range of 500 to 1000 centipoise (cp) after 90 minutes at pH 10 by simulation in a FANN viscometer at 275° F. (135° C.) and 212 rpm at 100 reciprocal second of shear.

12. The method of claim 11 wherein the aqueous liquid, cross-linkable organic polymer; and solution of zirconium cross-linking agent are contacted prior to their introduction into the subterranean formation.

13. The method of claim 11 wherein the subterranean formation is penetrated by a wellbore and wherein the method comprises (a) preparing a base gel by mixing the cross-linkable organic polymer with the aqueous liquid; (b) introducing the base gel into the wellbore; (c) simultaneously with or sequentially after, introducing the base gel into the wellbore, introducing the solution of the zirconium cross-linking agent into the wellbore; (d) permitting the base gel and the solution of zirconium cross-linking agent to react in the wellbore to form a cross-linked aqueous gel; and (e) introducing the cross-linked gel into the formation from the wellbore at a flow rate and pressure sufficient to create, reopen, and/or extend a fracture in the formation.

14. The method of claim 11 or 13 further comprising introducing proppant into the subterranean formation.

15. The method of claim 11 or 13 wherein the pH is in the range of 9-12.

16. The method of claim 15 wherein the temperature of the formation is in the range of 250-400° F. (121-204° C.).

17. The method of claim 16 wherein the temperature is in the range of 325-400° F. (163-204° C.).

18. The method of claim 11 wherein the amount of cross-linkable organic polymer present in the cross-linked gel is in the range of 0.1 to 1.2 weight %; the amount of zirconium cross-linking agent is in the range of 0.01 to 0.50 weight %.

19. The method of claim 18 wherein the amount of cross-linkable organic polymer present in the cross-linked gel is in the range of 0.25 to 0.75 weight %, and the amount of zirconium cross-linking agent is in the range of 0.05 to 0.25 weight %.

20. A method for plugging a permeable zone or leak in a subterranean formation which comprises introducing into said zone or said leak, (a) an aqueous liquid, (b) a cross-linkable organic polymer, and (c) a solution of a zirconium cross- linking agent which is produced by a process which comprises contacting a zirconium triethanolamine complex have a molar ratio of 1:2 to 1:5 of zirconium to triethanolamine with a mixture of polyols, which mixture comprises a hydroxyalkylated diamine and a hydrocarbon polyol wherein the molar ratio of zirconium to hydroxyalkylated diamine is 1:0.5 to 1:1, and the molar ratio of zirconium to hydrocarbon polyol is 1:0.5 to 1:1.5, and wherein the cross-linking composition has a cross-linking rate of 5-7 minutes generating viscosity in the range of 500 to 1000 centipoise (cp) after 90 minutes at pH 10 by simulation in a FANN viscometer at 275° F. (135° C.) and 212 rpm at 100 reciprocal second of shear.

21. The method of claim 20 wherein the aqueous liquid, cross-linkable organic polymer; and solution of zirconium cross-linking agent are contacted prior to their introduction into the subterranean formation.

22. The method of claim 20 wherein the solution of zirconium cross-linking agent and the cross-linkable organic polymer are introduced separately into the permeable zone or the site of the subterranean leak such that cross-linking occurs within the subterranean formation.

23. The method of claim 20 comprising (a) preparing a base gel by mixing a cross-linkable organic polymer with an aqueous liquid; (b) introducing the base gel into the into the permeable zone or the site of the subterranean leak; (c) simultaneously with or sequentially after, introducing the base gel into the into the permeable zone or the site of the subterranean leak, introducing the solution of zirconium cross-linking agent into the into the permeable zone or the site of the subterranean leak; (d) permitting the base gel and the cross-linking agent to react to form a cross-linked aqueous gel to plug the zone and/or leak.

24. The method of claim 20 or 23 wherein the pH is in the range of 9-12.

25. The method of claim 24 wherein the temperature of the formation is in the range of 250-400° F. (121-204° C.).

26. The method of claim 25 wherein the temperature is in the range of 325-400° F. (163-204° C.).

27. The method of claim 20 wherein the amount of cross-linkable organic polymer present in the cross-linked gel is in the range of 0.25 to 1.2 weight %; the amount of zirconium cross-linking agent is in the range of 0.01 to 0.50 weight %.

28. The method of claim 27 wherein the amount of cross-linkable organic polymer present in the cross-linked gel is in the range of 0.40 to 0.75 weight %, and the amount of zirconium cross-linking agent is in the range of 0.05 to 0.25 weight %.

* * * * *

UNITED STATES PATENT AND TRADEMARK OFFICE
CERTIFICATE OF CORRECTION

| | | |
|---|---|---|
| PATENT NO. | : 7,795,188 B2 | Page 1 of 1 |
| APPLICATION NO. | : 11/731405 | |
| DATED | : September 14, 2010 | |
| INVENTOR(S) | : Donald Edward Putzig | |

It is certified that error appears in the above-identified patent and that said Letters Patent is hereby corrected as shown below:

Title page, and Column 1, Line 1-3,
Item 54, the title should read --ZIRCONIUM-BASED CROSS-LINKER COMPOSITIONS AND THEIR USE IN HIGH PH OIL FIELD APPLICATIONS--.

Signed and Sealed this
Twenty-second Day of February, 2011

David J. Kappos
*Director of the United States Patent and Trademark Office*